US006819210B2

(12) United States Patent
Boynton et al.

(10) Patent No.: US 6,819,210 B2
(45) Date of Patent: Nov. 16, 2004

(54) STATIC MAGNETIC FIELD, METHOD OF CREATION, AND RESTING SURFACE THEREIN

(75) Inventors: Thomas Boynton, Floresville, TX (US); David M. Tumey, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 157 days.

(21) Appl. No.: 10/010,821

(22) Filed: Nov. 13, 2001

(65) Prior Publication Data

US 2003/0095022 A1 May 22, 2003

(51) Int. Cl.[7] ................................................ H01F 5/00
(52) U.S. Cl. .............................. 335/299; 600/9; 600/13
(58) Field of Search ........................ 335/299, 318–321, 335/216, 224; 600/9, 10, 13, 15; 324/318–321

(56) References Cited

U.S. PATENT DOCUMENTS

| 5,517,169 | A | * | 5/1996 | Laskaris et al. ............ 335/301 |
| 5,812,043 | A | * | 9/1998 | Gore et al. ................. 335/216 |
| 5,935,516 | A | | 8/1999 | Baugh |
| 6,042,531 | A | | 3/2000 | Holcomb |
| 6,048,302 | A | * | 4/2000 | Markoll ....................... 600/13 |
| 6,048,303 | A | | 4/2000 | Porter |
| 6,054,854 | A | * | 4/2000 | Kawamoto ................. 324/318 |
| 6,218,923 | B1 | * | 4/2001 | Laskaris et al. ............ 335/299 |
| 2002/0171425 | A1 | * | 11/2002 | Yui et al. .................... 324/318 |

OTHER PUBLICATIONS

Jarmo Ruohonen, "Coil Design for Real and Sham Transcranial Magnetic Stimulation," IEEE Transactions on Biomedical Engineering, vol. 47, No. 2, Jan. 2000.

Veit Schnabel et al, "Calculation of Electric Fields in a Multiple Cylindrical Volume Conductor Induced by Magnetic Coils," IEEE Transactions on Biomedical Engineering, vol. 48, No. 1, Jan. 2001.

P. Ravazzani, et al, "Optical Coil Design for Magnetic Stimulation of the Nervous System," Proceedings of the First Joint BMES/EMBS Conference, Oct. 13–16, 1999, Atlanta, Georgia.

Part II of unidentified book, study or report, with section entitled "Homogeneous Magnetic Fields," date, title, author & publisher unknown.

Beverly Rubik, et al., "Bioelectromagnetic Applications in Medicine," from unidentified web source; date =Mar. 22, 2000 or earlier; website unknown.

Institute of Technical Energy Medicine, Inc., "The Scientific Basis for Magnet Therapy: Analytical Research Report," from, apparently, item–bioenergy.com; date =Jul. 20, 2000 or earlier.

"Magnetic Field Therapy," Alternative Therapies, pp. 330–338; author, title, date, and publisher unknown.

Series of abstracts in response to search query at www-.biomednet.com/db/medline, no date.

Group of 3 abstracts from the journals Bioelectromagnetics and Int. J. Neuroscience, no date.

* cited by examiner

*Primary Examiner*—Lincoln Donovan
*Assistant Examiner*—Bernard Rojas

(57) ABSTRACT

A magnetic treatment system and method for generating a large uniform magnetic field to enhance the health of human subjects through exposure to the magnetic field. The system has narrow coils which allow excellent visibility to and from the subject being treated. The method of the invention provides for the heuristic adjustment of the various system parameters to ensure adequate uniformity, volume, and strength of the magnetic field. To facilitate comfort and convenience dining extended periods of treatment, the system also has various types of rusting surfaces within the volume of space containing the uniform magnetic field. Though there is no theoretical limit for the intensity of the uniform magnetic field generated by this invention, typical field strengths range from ten times the earth's magnetic held strength to forty times the earth's magnetic field strength.

9 Claims, 6 Drawing Sheets

Orthogonal View of Present Invention

Orthogonal View of Present Invention

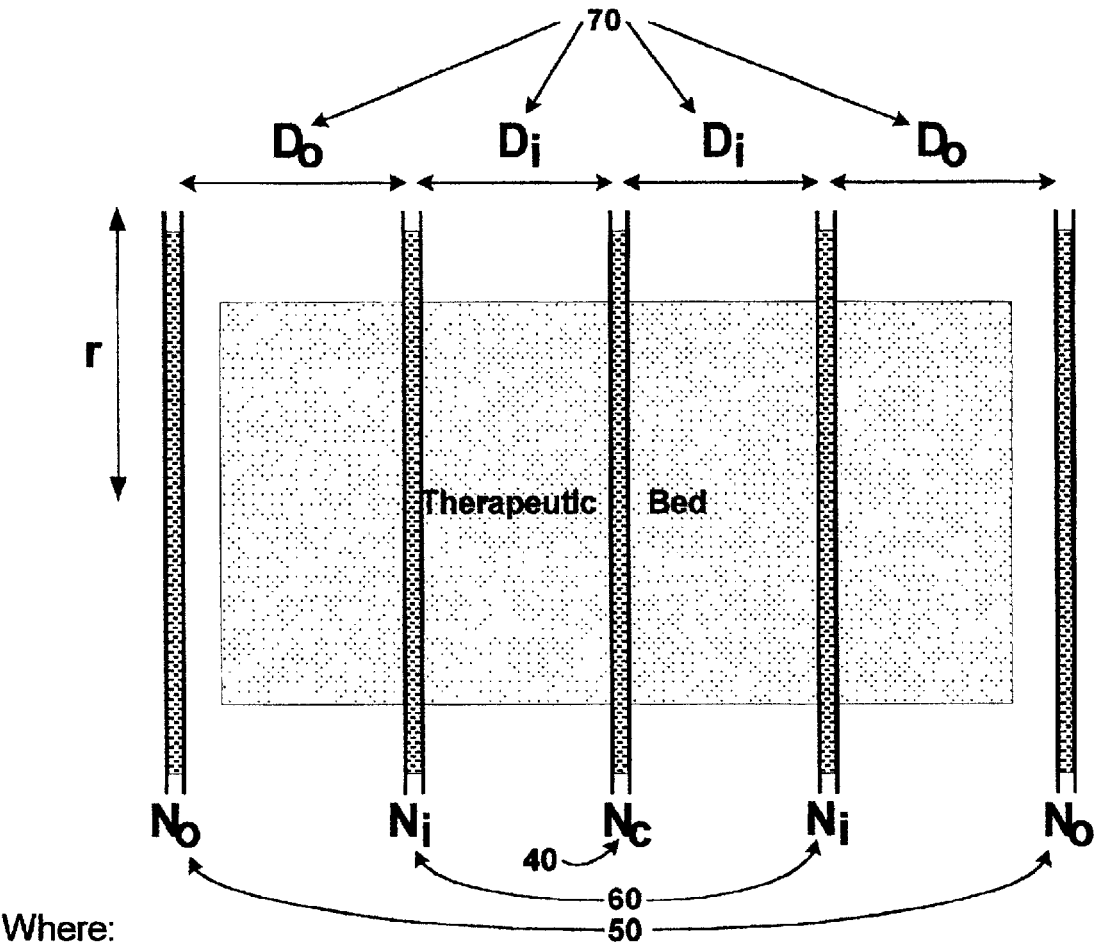

Where:

$D_o$ = Distance between each end coil and its adjacent coil $D_i$ = Distance between the center coil and each of its adjacent coils r = radius of each coil $N_o$ = Number of turns of wire on each end coil $N_i$ = Number of turns of wire on each coil adjacent to an end coil $N_c$ = Number of turns of wire on the center coil NOTE: All distances listed above are center to center distances FIG. 2
Overhead View of Coil Spacings (for 5 coil system)

Process for Developing an Acceptably Uniform Field in a Polycoil System

Overhead View of Coil Spacings
(for 5 coil system and for Traditional Helmholtz Pair)

Magnetic Field Strength of Longitudinal Component

Each curved line = change of 1 Gauss

34"/47.6" = 71% of diameter of patient surface has a substantially uniform (i.e., 4.5-5.5 Gauss) field strength 3-D Surface Map of Magnetic Field Strength

STATIC MAGNETIC FIELD, METHOD OF CREATION, AND RESTING SURFACE THEREIN

INTRODUCTION

This invention relates generally to devices and methods for generating volumes of space containing generally uniform static magnetic fields suitable for systemic treatment of an afflicted patient. More particularly, this invention relates to a device, and method of use therefor, which generates a substantially uniform static magnetic field in a sizeable volume of space defined in part by a plurality of DC electromagnetic coils, a method for systematically arranging and configuring these coils, and a patient supporting surface which may be placed therein and which an afflicted patient may be placed upon.

BACKGROUND OF THE INVENTION

Throughout history, human beings have lived in an analog, rather than a digital world. Neither the sun nor the sundial kept precise time, but both were more than sufficient to fix dinnertime. Uniform likely once meant one part in ten or twenty, or one part in fifty or one hundred. A slide rule was, at best accurate to one part in one thousand, and was used for all but the most precise engineering and scientific work of its day. Applicant doubts that the basic human physiology or biology has changed much from then.

Although scientists disagree regarding what causes the earth's magnetic field or the exact nature of the historical intensity changes of that field, there is general agreement that, in recent years, it has been decreasing. Some analysts conclude that the earth's magnetic field has decreased 5% per century for at least the last 1000 years. If this rate of decline has been occurring over the 6000 years of history recorded in the Bible, it would indicate that the earth's magnetic field at the time of Adam and Eve could have been as high as 20 gauss compared to the present 0.5 gauss geomagnetic field. Life spans recorded in the Biblical Chronology were at least an order of magnitude greater than they are today. Applicant believes that a more intense geomagnetic field may have been a contributory factor and that the recent measured decreases of geomagnetic field may be related to the increasing incidence of certain disease states. Research into the effects of magnetic fields upon living things began thousands of years ago and continues.

Recently, this research has primarily focused on the adverse effects of electromagnetic fields generated by A.C., and the therapeutic effects of permanent magnets used to treat specific localized afflictions. The fields of these magnets rapidly diminish with distance from the magnet. The actual field strength generated more than an inch or two from a typical permanent magnet, or a plurality of them is much weaker than the nominal strength of the magnet, and is quite nonuniform.

What appears to be a scholarly review of the history and current trends in biomagnetism appears at http://www.spot4u.com/post/doc.html. Extracts from this report appear below:

Bioelectromagnetics Applications in Medicine

PANEL MEMBERS AND CONTRIBUTING AUTHORS

Beverly Rubik, Ph.D.—Chair, Robert O. Becker, M. D., Robert G. Flower, M. S., Carlton F. Hazlewood, Ph.D., Abraham R. Liboff, Ph.D., Jan Walleczek, Ph.D.

Overview

Bioelectromagnetics (BEM) is the emerging science that studies how living organisms interact with electromagnetic (EM) fields All of the known frequencies of EM waves or fields are represented in the EM spectrum, ranging from DC (zero frequency) to the highest frequencies, such as gamma and cosmic rays. The EM spectrum includes x rays, visible light, microwaves, and television and radio frequencies, among many others. Moreover, all EM fields are force fields that carry energy through space and are capable of producing an effect at a distance.

Endogenous fields (those produced within the body) are to be distinguished from exogenous fields (those produced by sources outside the body). Exogenous EM fields can be classified as either natural, such as the earth's geomagnetic field, or artificial (e.g., power lines, transformers, appliances, radio transmitters, and medical devices). The term electropollution refers to artificial EM fields that may be associated with health risks.

It is possible that the effects (both beneficial and harmful) of exogenous fields may be mediated by alterations in endogenous fields. Thus, externally applied EM fields from medical devices may act to correct abnormalities in endogenous EM fields characteristic of disease states.

Medical Applications of Bioelectromagnetics

Bone Repair

Three types of applied EM fields are known to promote healing of nonunion bone fractures (i.e., those that fail to heal spontaneously):

Pulsed EM fields (PEMFs) and sinusoidal EM fields (AC fields).

DC fields.

Combined AC-DC magnetic fields tuned to ion-resonant frequencies (these are extremely low-intensity, physically nonthermal fields) (Weinstein et al., 1990).

Approval of the U.S. Food and Drug Administration (FDA) has been obtained on PEMF and DC applications and is pending for the AC-DC application. In PEMF and AC applications, the repetition frequencies used are in the ELF range (Bassett, 1989). In DC applications, magnetic field intensities range from 100 microgauss to 100 gauss (G), and electric currents range from less than 0.1 microampere to milliamperes (Baranowski and Black, 1987). FDA approval of these therapies covers only their use to promote healing of nonunion bone fractures, not to accelerate routine healing of uncomplicated fractures.

Efficacy of EM bone repair treatment has been confirmed in double-blind clinical trials (Barker et al., 1984; Sharrard, 1990). A conservative estimate is that as of 1985 more than 100,000 people had been treated with such devices (Bassett et al., 1974, 1982; Brighton et al., 1979, 1981; Goldenberg and Hansen, 1972; Hinsenkamp et al., 1985).

Regeneration

Animal research in this area indicates that the body's endogenous EM fields are involved in growth processes and that modifications of these fields can lead to modest regeneration of severed limbs (Becker, 1987; Becker and Spadero, 1972; Smith, 1967). Russian research and clinical applications, along with studies now under way in the United States, indicate that low-intensity microwaves apparently stimulate bone marrow stem cell division and may be useful in enhancing the effects of chemotherapy by maintaining the formation and development, or hematopoiesis, of various types of blood cells (Devyatkov et al., 1991).

The following studies are also relevant to the use of BEM for regeneration:

DC applications to promote rat spinal cord regeneration (Fehlings et al., 1992; Hurlbert and Tator, 1992).

Swedish work showing that BEM promotes rat sciatic nerve regeneration (Kanje and Rusovan, 1992; Rusovan and Kanje, 1991, 1992; Rusovan et al., 1992).

Immune System

In wound healing and regeneration, repair of soft tissue and reduction of collagenous tissue in scar formation; regrowth via blastemal (primitive cell) formation and increase in tensile strength of surgical wounds; alleviation of decubitus chronic ulcers (bedsores); increased angiogenesis (regrowth of vascular tissue such as blood vessels); and healing of recalcitrant (i.e., unresponsive to treatment) chronic venous ulcers.

For instance, a short-term, double-blind clinical trial of magnetic field therapy could be based on the protocol of Trock et al. (1993) for osteoarthritis of the knee or elbow. This protocol is as follows:

A suitable patient population is divided into treatment and control groups. Individual assigmnents are coded and remain unknown to patients, clinicians, and operators until treatment and assessment are complete.

Pretreatment clinical markers are assessed by clinicians or by patients themselves or both.

Treatments consist of 3 to 5 half-hour sessions each week for a total of 18 treatments over 5–6 weeks.

During treatment, each patient inserts the affected limb into the opening of a Helmholtz coil (a solenoid about 12 inches in diameter and 6 inches long) and rests while appropriate currents are applied to the coil via a preset program.

The treatment is noninvasive and painless; the patient feels nothing; there is no measurable transfer of heat to the patient.

The control group follows the same procedure except that, unknown to operator and patient, a "dummy" apparatus (altered internally so that no current flows in the coil) is used.

Patients' posttreatment clinical markers are assessed.

Appropriate data reduction (scoring of assessments, decoding of the treatment and control groups, and statistical analysis) is performed.

Clinical trials of BEM-based treatments for a variety of other conditions could follow a similar general outline.

In addition to the use of devices by practitioners, a plethora of consumer medical products that use magnetic energy are purported to promote relaxation or to treat a variety of illnesses. For example, for the bed there are mattress pads impregnated with magnets; there are magnets to attach to the site of an athletic injury; and there are small pellet-like magnets to place over specific points on the body. Most of these so-called therapeutic magnets, also called biomagnets, come from Japan. However, no known published journal articles demonstrating effectiveness via clinical trials exist.

BEM potentially offers a powerfull new approach to understanding the neuroendocrine and immunological bases of certain major medical problems (e.g., wound healing, cancer, and AIDS). However, substantial funding and time are required to perform the basic research needed in developing this approach."

For an example of a purportedly efficacious magnetic therapy device, applicant found the following; http://www.deslerent.com/magnets/12month.htm SUMMARY OF A 12-MONTH, DOUBLE-BLIND, CLINICAL TEST OF MAGNETIC MATTRESS PADS CARRIED OUT BY SAN-IKUKAI HOSPITAL, TOKYO COMMUNICATIONS HOSPITAL, AND KOUSEIKAI SUZUKI HOSPITAL BY DR. KAZUO SHIMODAIRA "The mattress pads used in this study were typical full-size pads containing 124 permanent ferrite magnets with magnetic field strengths of 750–950 gauss each. The pads themselves were made of two sheets of felt with the magnets sandwiched between them. The felt sheets were then wrapped in a cloth cover. The total number of subjects in this double blind clinical experiment was 431 (216 male, 215 female). 375 subjects were given magnetic pads, 56 were given non-magnetic pads. None of the 431 subjects knew which pad they were sleeping on. Subjects selected for the experiment were those with chief complaints related to: Neck and Shoulder pain, Back and Lower Back Pain, Back Pain (general), Lower Limb pain, Insomnia and Fatigue. To determine the presence of any side effects, blood pressure, hemoglobin, number of erythrocytes and number of leucocytes were examined before and after the use of the mattress pads. Besides blood sedimentation, and TP, COL, ALT, GOT, GPT, Na, and K were also examined, as were functions of the kidneys, liver, pancreas, and the entire circulatory system.

Results table

| SYMPTOM | CASES | POSITIVE RESULTS | (%) | NO RESULTS | (%) |
| --- | --- | --- | --- | --- | --- |
| Neck & Shoulder Pain | 66 | 47 | 71.2 | 19 | 28.8 |
| Back & Lower Back Pain | 76 | 61 | 80.3 | 15 | 19.7 |
| Back Pain (general) | 31 | 25 | 80.7 | 6 | 19.3 |
| Lower Limb Pain | 68 | 54 | 79.4 | 14 | 20.6 |
| Insomnia | 70 | 61 | 87.1 | 9 | 12.9 |
| Fatigue | 64 | 53 | 82.8 | 11 | 17.2 |

Out of 375 total subjects with symptoms, 301 (80.27%) reported positive results. 74 cases (19.73%) reported no results Time of Response The percentage of subjects who realized the effect of the magnetic mattress pad within 3 days: Neck and Shoulder pain 46.9%, Back and Lower Back Pain 50%, Back Pain (general) 38.7%, Lower Limb pain 54.4%, Insomnia 64.3% and Fatigue 57.8%. Out of 375 total subjects who slept on magnetic mattress pads, 200(53.3%) realized the effects within 3 days. Over 70% realized the effects within 5 Days.

Testing for side effects was conducted at the conclusion of the experiment. Symptoms such as tinnitus, headache, hearing problems, visual disturbances, vertigo, palpitation, perceptive abnormality, motor disturbance, fever, digestive disturbance, cutaneous symptoms, and other clinical symptoms to suggest any side effects were found to be totally absent. Extensive testing was also done before and after the experiment to check functions of the kidney, liver, pancreas, blood pressure, and circulatory system. No clinical symptoms were found to indicate any side effects whatsoever.

Conclusion

Dr. Shimodaira's conclusion of this year long study conducted in 3 of Japan's foremost hospitals: "The magnetized health mattress (pad) is proved to be effective on neck and shoulder pain, back and lower back pain, back pain, lower limb pain, insomnia and fatigue, and to have no side effects."

Applicant has so far been unable to locate any other report on this study. Another apparent problem with this device is the lack of uniformity in field strength. A veterinary magnet was evaluated. Magnetic field strength is measured in one of two units: 1 Tesla=$10^4$ (Gauss. The magnetic field strength of a Norfield's MAGNETIC hockwrap™ (for horses) measured at California Institute of Technology had field strength of 270 Gauss at the level of the pad and 1 Gauss at a distance of 1 cm from the pad. This article was located at http://www.hcrc.org/contrib/ramey/magnet.html Plainly, the mattress pad described above has anything other than a uniform static magnetic field. Further, the average field strength is likely to approximate 1 Gauss or less.

The generation of static magnetic fields of more than moderate size has also been a daunting task. Pairs of DC electric coils known as Helmholtz coils have long been known to be capable of generating limited volumes of space having uniform magnetic fields, as is well known in the art. However according to the prior art, these coils must comply with relatively stringent requirements. The coils must be of equal size, r, be identical, carry the same current, and be separated by the distance r. If those conditions are met, an axially uniform static magnetic field may be generated in some portion of the volume between the coils; this field is known to be substantially uniform along this axis.

Those machines known as NMR machines apparently have the ability to generate uniform magnetic fields over a volume having a radius on the order of 50 cm. However these fields are designed for the chemical analysis of inanimate samples, not for the possible systemic application of a uniform static magnetic field to a living subject.

From the foregoing several facts emerge. There are some reported therapeutic benefits from static magnetic fields. However there has been little use of large-scale substantially uniform static magnetic fields, as their generation has been problematic at best. The primary method of creating any semblance of such a field has been through the Helmholtz coil, which, a] is subject to restrictive conditions, and b] generates an axially substantially uniform field in a relatively small volume of space.

U.S. Pat. No. 5,935,516, to Baugh, teaches an air-tight chamber for placement of plants, animals, raw materials, and other items. The reference also teaches the use of a single shielded coil surrounding or lining the inside of the chamber to establish an AC-powered, variable magnetic field within the chamber of a predetermined strength and orientation. There is no indication that the reference, which teaches oscillating the magnetic field at a frequency of 0.5 to 30 Hz, is operable to produce a substantially uniform static magnetic field. Moreover, the apparatus taught is not advantageously disposed for use on patients because of the difficulty of entering or exiting the chamber and because the use of a single coil wound about the entire length of the chamber would tend to obstruct access to the patient.

What is needed is an apparatus for generating a large-scale uniform static magnetic field having a substantial volume large enough to accommodate a resting surface capable of comfortably accommodating an adult human being, which could be contained there within. What is also needed is a systemized method for arranging and configuring DC powered coils to create such fields. It is towards filing these needs that the present invention is directed.

BRIEF DESCRIPTION OF THE DRAWINGS

FIG. 2 is a view of the present invention demonstrating the intervals and naming conventions utilized in coil spacing.

SUMMARY OF THE INVENTION

Figure 1:
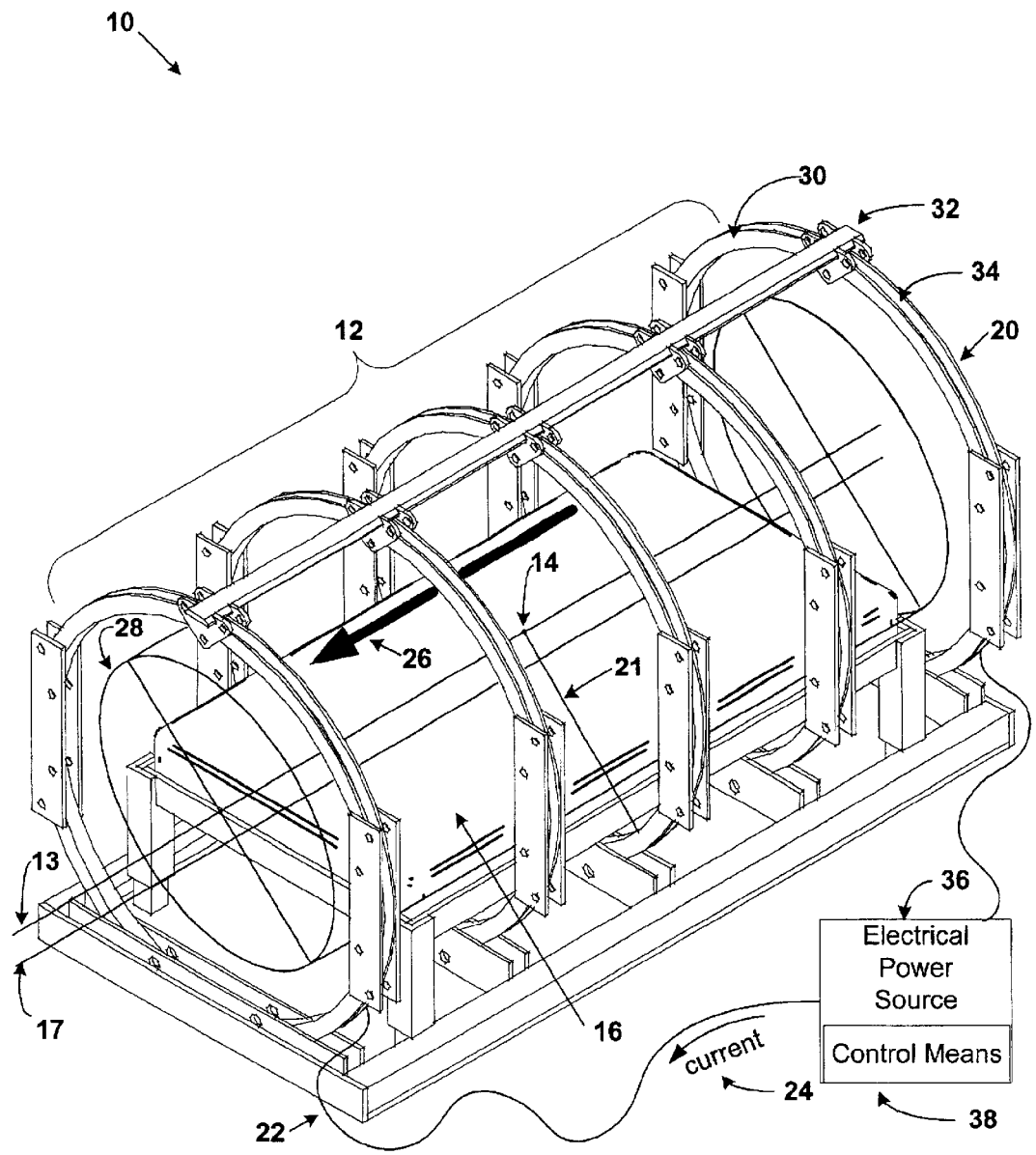
FIG. 1 is an orthogonal of the present invention

In brief, the present invention comprises a substantially uniform static magnetic field of a sufficient volume within which a non-ferrous resting surface may be located, and a method of analytically arranging and configuring coils so as to generate a large volume, substantially uniform static magnetic field with easy access for ingress and egress to/from the resting surface within the field. While it is true that a substantially uniform field could be created using a solenoid comprising a totally enclosed cylindrical volume with wire wound evenly over the entire surface of the cylinder, this would not provide the easy access into and out of the volume containing the substantially uniform field of the present invention which provides large open spaces between the narrow wire loops which generate the field. The resting surface is located within a plurality of large coils of conductive wire. These coils would have a common longitudinal axis, and would therefore be substantially parallel. The coils receive carefully controlled D.C., and therefore generate a magnetic field perpendicular to the coils, and parallel to their longitudinal axis. The resting surface may be located within the volume of this substantially uniform static magnetic field. A presently desirable field strength for this field is from about 5 Gauss to about 20 G, as desired.

The resting surface would be substantially parallel to this axis, and, accordingly, substantially perpendicular to the coils. Many design options exist. For example, an individual in good health, who wishes to remain in that states could use the present invention. In that case, the sleeping surface could comprise a futon, bed, or other sleeping surface.

If the patient required kinetic therapy, or other treatment, a therapeutic or hospital bed, adapted as needed with products from such manufacturers, such as assignee, Kinetic Concepts, Inc. of San Antonio Tex., U.S.A., could also be employed. Similarly, if the patient were bedridden, or confined to bed for a substantial length of time, a reduced pressure therapeutic mattress could be employed. Because water is substantially transparent to magnetic fields of this nature, a water filled mattress could also be used as the sleeping surface. Additionally, given the physics involved, the sleep surface could also be oriented to have some or all of the sleep surface sloped, for therapeutic benefits, without adversely affecting the effects received from the magnetic field provided. Even surfaces with limited amounts of ferromagnetic materials such as steel could be employed as long as some localized degradation in the field uniformity can be tolerated in areas close to the ferro-magnetic material.

The method provided allows several parameters to be established. These parameters include coil radius, overall length of the coil assembly, average field strength, and degree of uniformity. Given these parameters, the number of turns, the amperage, and the spacing of the pairs of the coils can be varied, until an acceptable solution is reached; thereafter the embodiment can be manufactured, and assembled, in accordance with the solution provided by the method. This method may be employed for an assembly having any number of coils greater than two.

Accordingly, an object of the present invention is to provide a means of generating a substantially uniform static magnetic field having a significant volume.

Another object of the present invention is to provide a systematic means of arranging and configuring DC coils so as to create a substantially uniform magnetic field having a significant volume.

A further object of the present invention is to provide a resting surface that is located within a substantially uniform static magnetic field generated by a plurality of DC coils, Yet another object of the present invention is to provide a method of providing a substantially constant static magnetic field to a person placed on a resting surface disposed within the field generating DC coils.

A still further object of the present invention is to provide a systematic method of determining the spacing and configuration of DC coils needed to provide a generally uniform static magnetic field for a predetermined volume of space.

These and still further objects as shall hereinafter appear are readily fulfilled by the novel apparatus of the present invention in a remarkably unexpected manner as will be readily discerned from the following detailed description of an exemplary embodiment thereof especially when read in conjunction with the accompanying drawings in which like parts bear like numerals throughout the several views.

DETAILED DESCRIPTION OF THE PREFERRED EMBODIMENTS

As shown in FIG. 1, the embodiment, referred to throughout by the general reference 10, comprises magnetic field generating means 12, having a longitudinal axis 13 having a midpoint 14. In most uses of this embodiment a secured resting means 16, having a longitudinal axis 17, oriented so that axes 13, 17 are substantially parallel, in a manner more fully described below will prove highly desirable. Means 12 comprises a plurality of substantially circular coils 20. Coils 20 each have a radius 21, and a given number of turns of copper wire 22 which, when direct current 24 is applied thereto, generate static magnetic field 26. Coils 20 define a volume 28, which is substantially cylindrical in shape, about longitudinal axis 13.

Coils 20 comprise housing 30, support 32, wire 34, power means 36, and control means 38. Coils 20 are arranged in a particular manner, as is shown in FIG. 2. Coils 20 are divided into Inner coil or coils 40, outer coils 50, and intermediate coils 60. While coils 20 need not be symmetrical about the midpoint 14 of the longitudinal axis 13, such will be assumed during the balance of this description of the preferred embodiment 10.

The inner coil, or coils 40 are longitudinally symmetrical about point 14. Therefore, if a single coil 40 is employed, its transverse axis is symmetrical about point 14. Outer coils 50 and intermediate coils 60 are arrayed about coil 40 in the manner directed by the method portion of the present invention.

Figure 3:
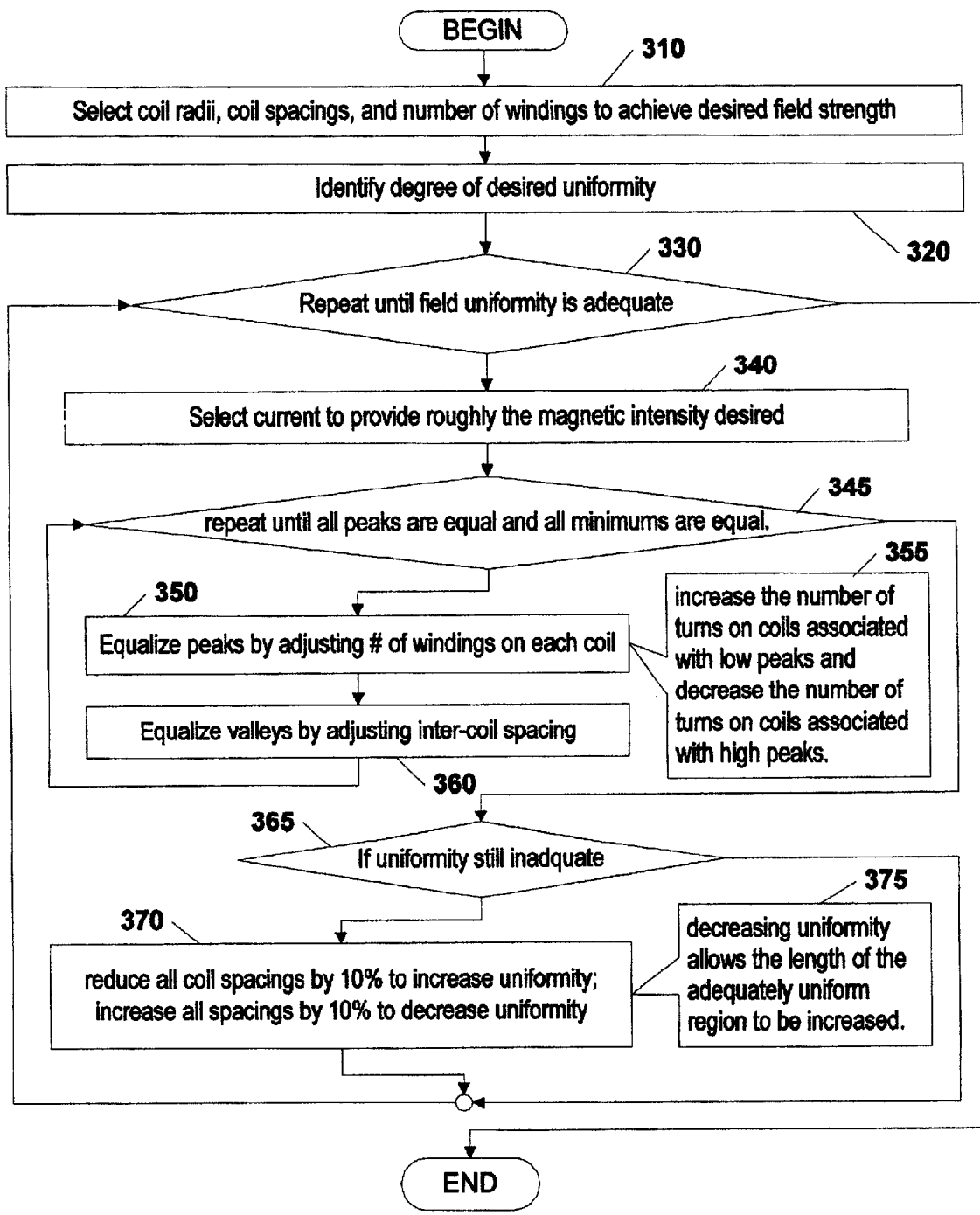
FIG. 3 is a flow chart of the process used to arrange and configure coils in the present invention.

The method portion of the present invention uses a variety of parameters about coils 20. The parameters include radius 21, number of turns of wire 22, current 24, as shown on FIG. 1, and effective interval 70, as shown on FIG. 2. FIG. 3 provides a flowchart of a process for identifying parameters that will yield an acceptably uniform field in a polycoil system. In block 310, identify the magnetic strength and spatial parameters for the desired uniform magnetic field. Using standard physics algorithms, select coil radii, coil spacings, and number of windings on each coil to achieve the desired field strength. In block 320, identify the degree of desired uniformity. In other words, determine the desired total variation between maximum and minimum axial magnetic field intensity. In block 340, set the current that is supplied to the coils to a value that provides approximately the amount of magnetic intensity desired.

Figure 4:
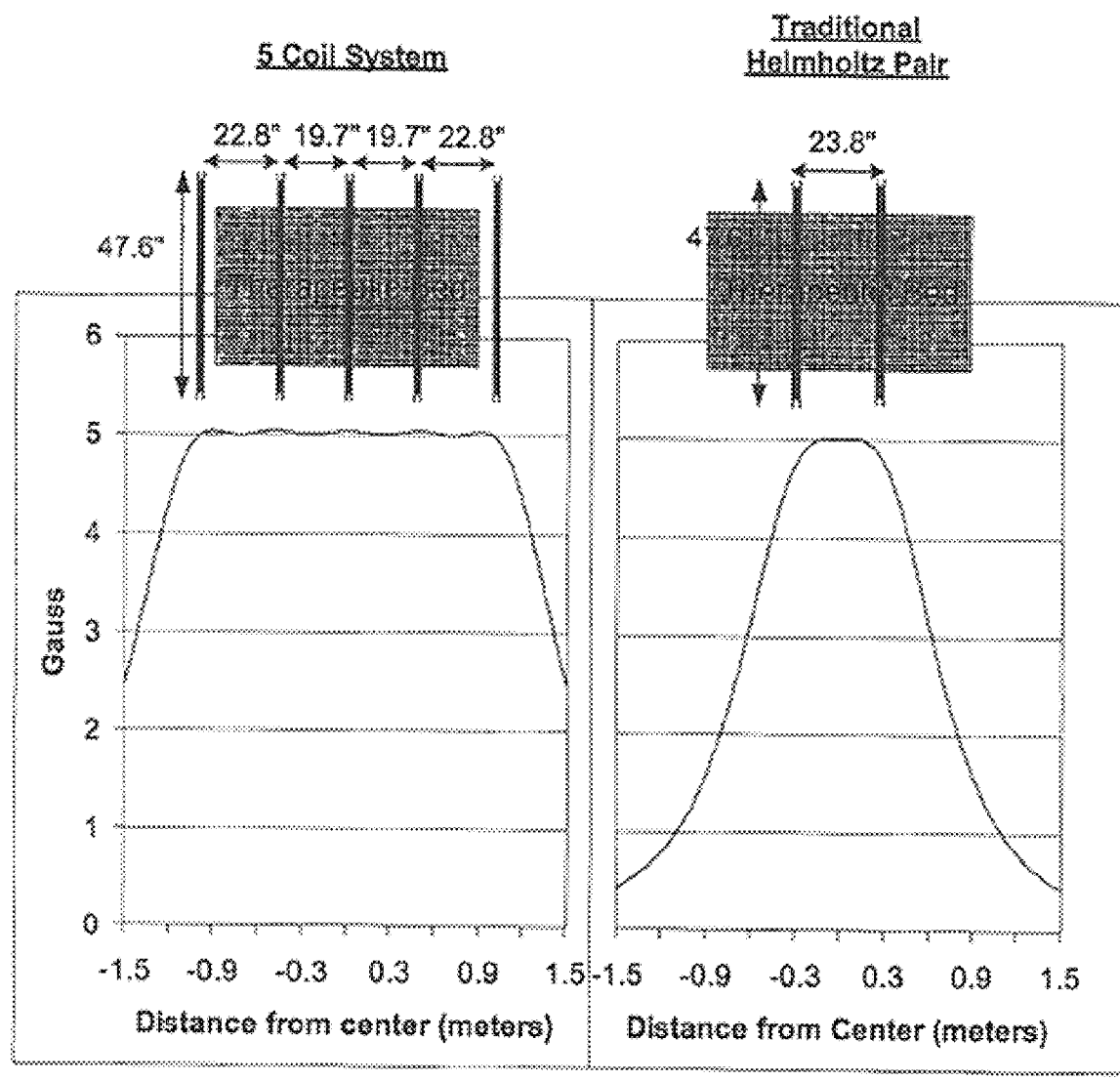
FIG. 4 is an axial magnetic field strength graph of the device of Example I with superimposed coil locations.

In block 350, adjust the number of windings on each coil until the magnetic intensity peaks corresponding to each of the coils is equal. (FIG. 4 illustrates a magnetic intensity curve for a five coil system.) As further illustrated in block 355, this can be done by increasing the number of turns on coils associated with low peaks and decreasing the number of turns on coils associated with high peaks. In block 360, adjust the distance between the coils in order to bring all of the minimum points in the magnetic intensity curve to the same level. As shown in block 345, the processes illustrated in blocks 350–360 are repeated until all peaks are equal and all minimums are equal.

If, in block 365, the uniformity is still inadequate, then in block 370, reduce all coil spacings by 10% to increase uniformity or increase spacings by 10% to decrease uniformity. As illustrated in block 375, the more nonuniformity tolerated, the longer the tolerably magnetically uniform region can be. As shown in block 330, the processes illustrated in blocks 340 through 375 are repeated until the desired uniformity is achieved.

The process steps of FIG. 3 are illustrative. A computer program that can calculate or simulate the magnetic field of a polycoil system may be used, in conjunction with iterative or brute formula-solving techniques, to determine the appropriate parameters (e.g., coil radii, coil spacing, number of windings, current) that will achieve the desired uniformity.

The following conditions have been found to be true when using the present invention to generate field strength of between 2 and 20 Gauss. First, the minimum width of substantial uniformity is one hundred twenty five percent (125%) of the coil radius "r". Second individual coil separations, except for the inner coil, should range from ½ to 2/1 r and more preferably should range from 2/3 to 3/2 r. Third, the magnetic output of any coils is a direct function of the product of the current and the number of turns for a given coil. Fourth, each pair of coils should be symmetrical. An Illustrative example follows:

EXAMPLE

Arrange five coils having a radius of 23.8" as shown in FIG. 2. Space the intermediate coils 19.7" to the left and right of the inner coil. Space one outer coil 22.8" to the left of the left-most intermediate coil, and space a second outer coil 22.8" to the right of the right-most intermediate coil. Apply 82 turns or windings of 12-gauge wire to the inner coil, 85 turns to each of the intermediate coils, and 135 turns to each of the outer coils. Apply sufficient current to generate a field strength of approximately 5 Gauss along the longitudinal axis 13 of the magnetic field. This produces a substantially uniform magnetic field as illustrated by the magnetic field curve of FIG. 4.

FIG. 4 also illustrates, for comparison, the magnetic field curve for a traditional Helmholtz pair. As can be seen, the present invention, unlike the traditional Helmholtz pair, is capable of achieving a substantially uniform static magnetic field over a volume long and wide enough to substantially encompass the human body.

Figure 5:
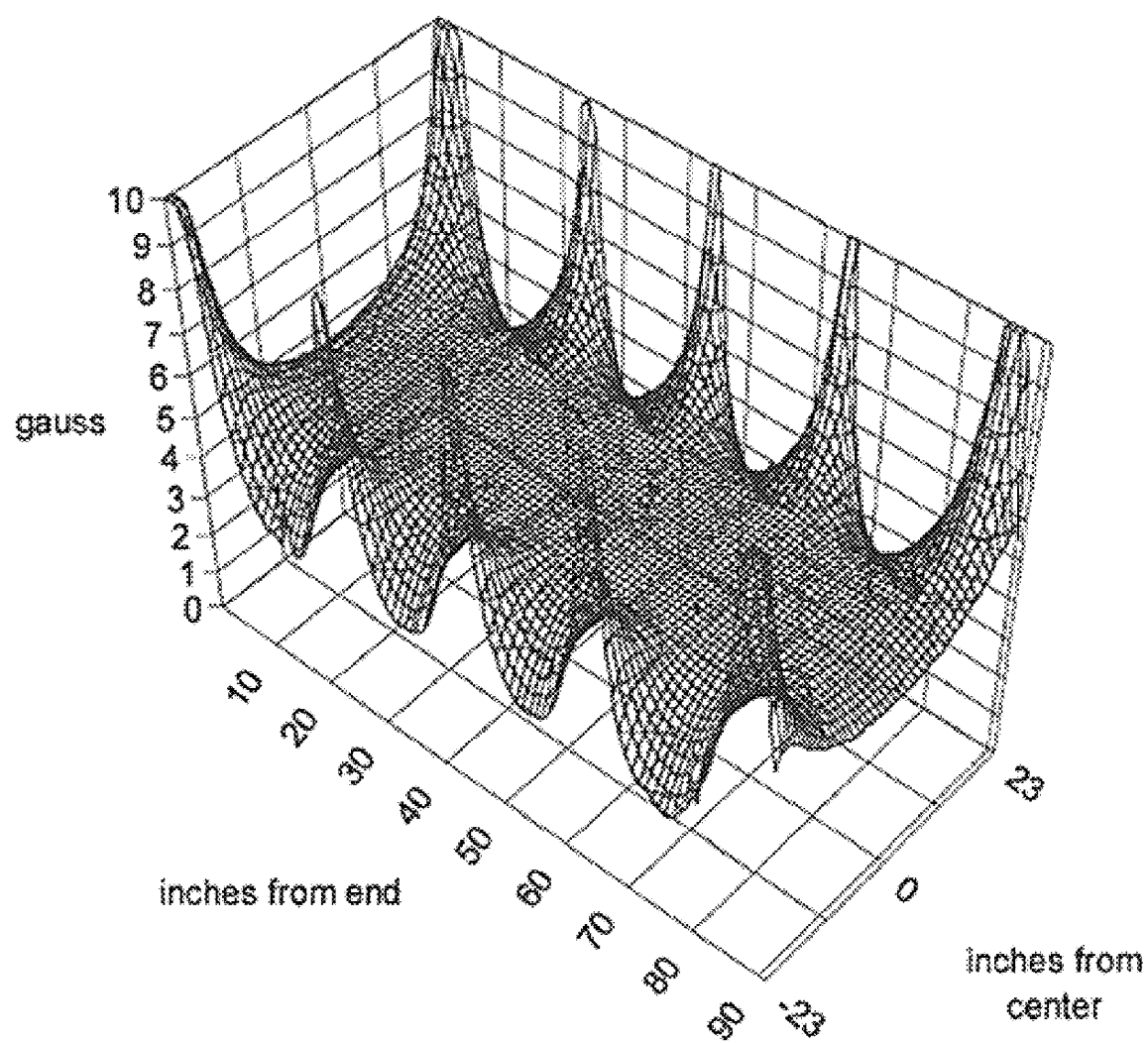
FIG. 5 is a three dimensional field strength graph of the device of Example I both on and off axis on any plane containing the axis.
Figure 6:
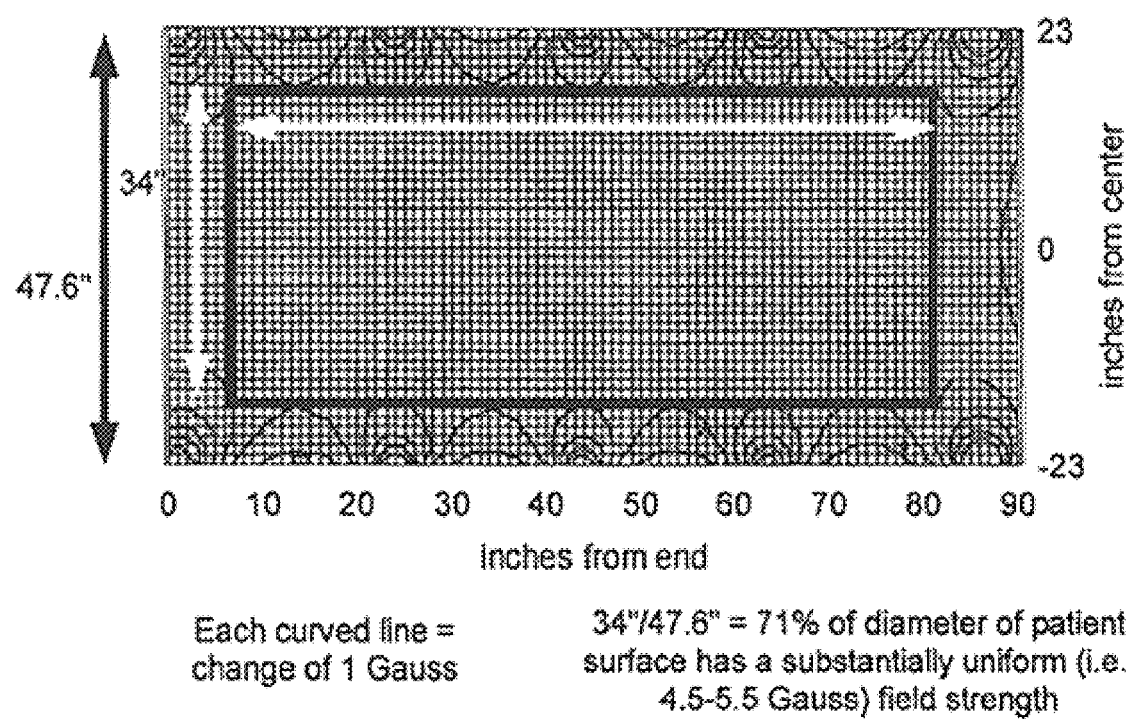
FIG. 6 is a two dimensional field strength graph of the device of Example 1 showing the area of essential field uniformity.

FIG. 5 illustrates the resulting field strength, in gauss, of the longitudinal magnetic field as a function of distance from the center and inches from one end of the magnetic field generating means 12. FIG. 6 also illustrates the field strength using a 3-D surface map where the curved lines represent the boundaries between field strengths of 2.5 Gauss to 3.5 Gauss, 3.5 Gauss to 4.5 Gauss, 4.5 Gauss to 5.5 Gauss, and so on. In this example, the substantially uniform region depicted has a magnetic field strength of between 4.5 and 5.5 Gauss and a width equal to approximately 71% of the diameter of the coils. A rectangular region depicted by a dark-bordered box illustrates how the present invention can be used to apply a substantially uniform magnetic field to a human body.

It should be noted that different iterations of the heuristic of FIG. 3 can produce different spacing, coil winding, and voltage level parameters to achieve substantially the same result. For example, the inventors believe that a substantially uniform magnetic field of substantially equivalent strength can be produced using the same distance and turns ratios but with 8-gauge wire instead of 12-gauge wire and fewer turns on each coil (i.e., reducing each coil's number of windings by a proportional amount). The inventors believe that this change to the configuration would significantly reduce the voltage required to produce current sufficient to generate the field strength of the above example.

Although the invention has been described in detail with reference to a certain illustrated embodiment, variations and modifications exist within the scope and spirit of the present invention as described and defined in the following claims.

Accordingly, the following is claimed:

1. An apparatus for treating a human body through application of a static magnetic field, comprising:
   a plurality of electrically conductive coaxial coils arranged about a common longitudinal axis, wherein said coaxial coils are positioned along a length of said common longitudinal axis;
   an elongate support surface having a cushion for supporting a human body thereon, said support surface being generally parallel to said common longitudinal axis and offset beneath said common longitudinal axis, such that a human body supported thereon tends to be positioned lengthwise along said length of said common longitudinal axis;
   a source of direct current electricity, operably connectable to said coils to conduct direct current through said coils, thereby generating a static magnetic field along said length of said common longitudinal axis; the strength of said field along said length of said common longitudinal axis being in the range of from five to twenty Gauss.

2. A treating apparatus as in claim 1, wherein said length is at least as long as the distance between the head and waist of the human body, inclusive.

3. A treating apparatus as in claim 1, wherein said coils are spaced equidistantly along said length of the common longitudinal axis.

4. A treating apparatus as in claim 1, wherein mid a first and second of said coaxial coils have a radius, and said first and second coils are separated by a separation distance in the range between half the radius and twice the radius.

5. A treating apparatus as in claim 1, wherein each of said coaxial coils has a radius of approximately "r", and each of said coils are separated by a distance in the range between half r and twice r.

6. An apparatus for enhancing the health of a human body through application of a static magnetic field, comprising:
   a plurality of electrically conductive coaxial coils arranged about a common longitudinal axis, wherein:
   (a) said coaxial coils are spaced equidistantly along a length or said common longitudinal axis,
   (b) said length is at least as long as the distance between the head and feet of the human body, inclusive,
   (c) each of said coils has a radius, and (d) each of said coils are separated distance in the range between half the radius and twice the radius;
   an elongate support surface having a cushion for supporting a human body thereon, said support surface being generally parallel to said common longitudinal axis and offset beneath said common longitudinal axis, such that a human body supported thereon tends to be positioned lengthwise along said length of mid common longitudinal axis;
   a source of direct current electricity, operably connectable to said coils to conduct direct current through said coils, thereby generating a static magnetic field along said length of said common longitudinal axis; the strength of said held along said length of said common longitudinal axis being in the range of from five to twenty Gauss.

7. A treating apparatus as in claim 6, wherein each of said coils receives the same amount of direct current.

8. A treating apparatus as in claim 6, wherein each of said coils comprise copper wire windings.

9. The apparatus of claim 8, wherein said resting surface is operable to support an afflicted human patient and to provide said magnetic field to said patient for a period of dine in excess of five hours.

* * * * *